US010145841B2

United States Patent
Chung et al.

(10) Patent No.: US 10,145,841 B2
(45) Date of Patent: Dec. 4, 2018

(54) METHOD FOR DETECTING ANTIGEN, AND APPARATUS USING SAME

(71) Applicant: NANOENTEK, INC., Seoul (KR)

(72) Inventors: Chan Il Chung, Seoul (KR); Chang Seop Lee, Ansan-Si (KR); Jeoung Ku Hwang, Ansan-Si (KR); Jong Sik Jeong, Goyang-Si (KR)

(73) Assignee: NANOENTEK, INC., Seoul (KR)

( * ) Notice: Subject to any disclaimer, the term of this patent is extended or adjusted under 35 U.S.C. 154(b) by 389 days.

(21) Appl. No.: 14/379,664

(22) PCT Filed: Feb. 20, 2013

(86) PCT No.: PCT/KR2013/001340
§ 371 (c)(1),
(2) Date: Aug. 19, 2014

(87) PCT Pub. No.: WO2013/125855
PCT Pub. Date: Aug. 29, 2013

(65) Prior Publication Data
US 2015/0024513 A1    Jan. 22, 2015

(30) Foreign Application Priority Data

Feb. 20, 2012 (KR) .................. 10-2012-0017039

(51) Int. Cl.
*G01N 33/543* (2006.01)
*G01N 33/53* (2006.01)

(52) U.S. Cl.
CPC ....... *G01N 33/54306* (2013.01); *G01N 33/53* (2013.01); *G01N 33/543* (2013.01)

(58) Field of Classification Search
None
See application file for complete search history.

(56) References Cited

U.S. PATENT DOCUMENTS

2006/0246601 A1* 11/2006 Song ............... G01N 33/54366
436/514
2007/0287147 A1    12/2007 Nagamune et al.

FOREIGN PATENT DOCUMENTS

KR    1020060126964 A    12/2006
KR    1020080012852 A    2/2008
(Continued)

OTHER PUBLICATIONS

Chin et al., Microfluidics-based diagnostics of infectious diseases in the developing world, Nature Medicine, vol. 17, No. 8, Published online Jul. 31, 2011, pp. 1015-1019.*

(Continued)

*Primary Examiner* — Rebecca L Martinez
(74) *Attorney, Agent, or Firm* — Clark & Elbing LLP; Susan M. Michaud

(57) ABSTRACT

The present invention provides a method for detecting an antigen in an analysis sample, the method including: (a) contacting an analysis sample with a detection antibody with which a marker generating a detectable signal is combined and which specifically binds to the antigen; (b) contacting a capture antibody with the resultant product of step (a), the capture antibody specifically binding to an antigen to be detected; (c) contacting the detection antibody, with which the marker generating a detectable signal is combined, with a reference substance which is bound to a surface of a solid substrate and which includes an epitope to which the detection antibody specifically binds; (d) measuring signals generated from the markers of the resultant product of step (b) and the resultant product of step (c); and (e) analyzing the measured signals to determine the presence or absence and amount of the antigen in the analysis sample. The method for detecting an antigen of the present invention can control the flow and the reaction time of an analysis sample, thereby improving sensitivity and minimizing the influences by the (Continued)

concentration of the analysis sample or the temperature of the detection reaction, and thus improving stability, reliability, and reproducibility of data, when compared with the conventional method for detecting an antigen. Accordingly, the method and apparatus for detecting an antigen of the present invention can be easily operated without specialized skills, thereby instantly obtaining the presence or absence and amount of detection antigen in the analysis sample through on-site diagnosis.

15 Claims, 15 Drawing Sheets

(56) References Cited

FOREIGN PATENT DOCUMENTS

| WO | WO-92/22797 A2 | 12/1992 |
| WO | WO-01/13116 A1 | 2/2001 |
| WO | WO-03/058242 A2 | 7/2003 |

OTHER PUBLICATIONS

International Search Report for PCT/KR2013/001340, dated Jul. 3, 2013 (7 pages).

* cited by examiner

METHOD FOR DETECTING ANTIGEN, AND APPARATUS USING SAME

CROSS-REFERENCE TO RELATED APPLICATIONS

This application is the U.S. National Phase of International Patent Application No. PCT/KR2013/001340, filed Feb. 20, 2013, which claims priority from Korean Patent Application No. 10-2012-0017039, filed on Feb. 20, 2012, in the Korean Intellectual Property Office.

TECHNICAL FIELD

The present invention relates to a novel method for detecting an antigen and an apparatus using the same.

BACKGROUND ART

The importance of the development of antigen detecting methods which enable prompt and simple measurement of a subject of analysis (e.g., antigen) among complicated samples and provide high reliability on measurement values is growing bigger and bigger. For example, the point of clinical diagnosis in the hospital emergency is that an unskilled technician can promptly and accurately check a patient's condition by performing complicated chemical or immunochemical analyses. These analyses are generally conducted by hospital staff or nurses who are not trained as a clinical chemist. Current clinical diagnosis systems in which blood samples are transferred to the hospital laboratory and then analyzed are not suitable when prompt laboratory findings are requested. Therefore, the measurement methods, in which analysis results can be provided in a short time and staff and equipment for conducting analyses are suitable for the request in the hospital diagnosis system, are required.

As the existing antigen detecting method, immunoassay is mainly used. Particularly, the immunoassay is generally used in detecting items of tumor markers. The immunoassay uses an antigen-antibody reaction, and can detect a desired material by using an antibody selectively binding to a material to be detected. The kinds and principles of representative immunoassays are as follows. Although the using methods and specific reaction conditions may be slightly different according to organs, basic principles thereof are almost the same as each other.

Particle immunoassay is a test that uses agglutination occurring by the binding of antigen and antibody. In most cases, the antigen or antibody is bound to latex, gelatin or the like, and this particle reacts to show agglutination, which is then measured. The measurement of agglutination may be made by measuring the absorption degree of light through turbidimetry or the scattering degree of light through nephelometry.

Enzyme immunoassay (EIA) is a test that uses an enzyme reaction to measure the binding of antigen and antibody. In most cases, an enzyme is previously bound to an antibody which binds to a material to be measured, to cause an antigen-antibody reaction. After that, a substrate is put into the bound enzyme to cause an enzyme reaction. Examples of a frequently used enzyme are alkaline phosphatase, horseradish peroxidase, β-galactosidase, etc. The products from the enzyme reaction are mostly materials having colors, which are measured by a spectrophotometer.

Radioimmunoassay is a test that uses radioisotopes to measure the binding of antigen and antibody. Radioisotopes are materials that are physically unstable, resulting in natural radioactive decay, and thus changed into stable materials, and produce radiation in this process. The radioisotopes are bound to a material, like a material to be measured, or an antibody reacting with the material to be measured, causing an antigen-antibody reaction. After the reaction is ended, the amount of radiation released from the reaction material is measured, thereby calculating the concentration of a desired material. The radioisotopes that are mostly used are $^{125}$I, $^{131}$I, $^{3}$H, $^{14}$C, $^{32}$P, etc. The radioimmunoassay had mostly been used in the past, but the use thereof has been decreasing since there is a risk of using a radioactive material and chemiluminescence immunoassay and the like have been developed.

Fluorescence immunoassay is a test that uses a fluorescence reaction to measure the binding of antigen and antibody. The fluorescence reaction refers to a reaction in which a molecule of a fluorescent material is excited when the fluorescent material absorbs a particular wavelength of light, and releases light having a different wavelength from the absorbed light when recovered to its original state. In the case where the fluorescence reaction is used for immunoassay, the fluorescent material is bound to a material, like a material to be measured, or an antibody reacting with the material to be measured, causing an antigen-antibody reaction. After the antigen-antibody reaction, the projection of light that has such a wavelength to cause a fluorescence reaction leads to the fluorescence in proportion to the amount of fluorescent material, and the amount of fluorescent material is used to calculate the concentration of the material to be measured.

Chemiluminescence immunoassay is a test that uses chemiluminescence to measure the binding of antigen and antibody. Chemiluminescence is the emission of light while the excited chemiluminescent material returns to the ground state, and is different from fluorescence in that the energy used to excite a molecule is not light but a chemical reaction. In the case where the chemiluminescence is used for immunoassay, the chemiluminescent material is bound to a material, like a material to be measured, or an antibody reacting with the material to be measured, causing an antigen-antibody reaction, in the same manner as other methods. After the reaction, a necessary chemical reaction is caused, and then the degree of luminescence emitted is measured, thereby calculating the concentration of material to be measured therefrom. Representative examples of the luminescent material are luminol, isoluminol, acridinium ester, etc.

The antigen detecting method which is to be used herein is based on Fluorescence immunoassay, and has been developed in order to overcome a problem of the conventional Fluorescence immunoassay in that reproducibility and reliability of data are poor since the measurement value of antigens is changed depending on the concentration of the sample and the reaction temperature. Accordingly, the present inventors have attempted to establish an antigen detection system which allows on-site diagnosis and is not interrupted by the concentration of a sample to be analyzed and the reaction temperature, based on Fluorescence immunoassay using an antigen-antibody reaction.

Throughout the entire specification, many papers and patent documents are referenced and their citations are represented. The disclosures of cited papers and patent documents are entirely incorporated by reference into the present specification, and the level of the technical field within which the present invention falls and details of the present invention are explained more clearly.

DETAILED DESCRIPTION OF THE INVENTION

Technical Problem

The present inventors have endeavored to develop a novel method for detecting an antigen. As a result, the present inventors have developed a method in which the same detection antibodies are bound to a test zone and a reference zone by binding a reference substance, which includes the same epitope as an antigen to be detected, to the reference zone, thereby more accurately detecting the presence or absence and amount of antigen, unlike the conventional method in which different detection antibodies are bound to the test zone and the reference zone to detect an antigen specifically binding to only the test zone. The present inventors have verified that, through the detection method of the present invention, the flow of an analysis sample and the reaction time are controlled, thereby improving reaction sensitivity and minimizing the influences by the concentration of the analysis sample or the temperature of the detection reaction, and thus improving stability, reliability, and reproducibility of data, when compared with the conventional method for detecting an antigen, and have completed the present invention.

Accordingly, an aspect of the present invention is to provide a novel method for detecting an antigen.

Another aspect of the present invention is to provide a novel apparatus for detecting an antigen.

Other purposes and advantages of the present invention will become clarified by the following detailed description of invention, claims, and drawings.

Technical Solution

In accordance with an aspect of the present invention, there is provided a method for detecting an antigen in an analysis sample, the method including:

(a) contacting an analysis sample with a detection antibody with which a marker generating a detectable signal is combined and which specifically binds to the antigen;

(b) contacting a capture antibody with the resultant product of step (a), the capture antibody specifically binding to an antigen to be detected;

(c) contacting the detection antibody, with which the marker generating a detectable signal is combined, with a reference substance which is bound to a surface of a solid substrate and which includes an epitope to which the detection antibody specifically binds;

(d) measuring signals generated from the markers of the resultant product of step (b) and the resultant product of step (c); and (e) analyzing the measured signals to determine the presence or absence and amount of the antigen in the analysis sample.

The present inventors have endeavored to develop a novel method for detecting an antigen. As a result, the present inventors have developed a method in which the same detection antibodies are bound to a test zone and a reference zone by binding a reference substance, which includes the same epitope as an antigen to be detected, to the reference zone, thereby more accurately detecting the presence or absence and amount of antigen, unlike the conventional method in which different detection antibodies are bound to the test zone and the reference zone to detect an antigen specifically binding to only the test zone. The present inventors have confirmed that, through the detection method of the present invention, the flow of an analysis sample and the reaction time are controlled, thereby improving reaction sensitivity and minimizing the influences by the concentration of the analysis sample or the temperature of the detection reaction, and thus improving stability, reliability, and reproducibility of data, when compared with the conventional method for detecting an antigen.

The method for detecting an antigen is a method for measuring the presence or absence and amount of antigen present in an analysis sample. When the analysis sample is human blood plasma, i) since a reference substance bound to a reference zone cannot be a human derived peptide or a substance capable of binding therewith, there is a limit in selecting the reference substance; ii) since different detection antibodies are bound to the test zone and the reference zone, the detection result may vary depending on the affinity to antigen of each antibody; iii) since, in the case where the analysis sample has a high concentration, the detection antibody of the test zone continuously binds to the reference zone at a uniform level regardless of the saturation degree of the detection antibody bound to the test zone, the ratio value of intensity of the measurement signal of the test zone/the signal of the reference zone is not constant; and iv) since the antigen-antibody reaction is basically used, the influence by the temperature, which is incidentally problematic, cannot be ruled out. Considering these problems, the present inventors have endeavored to develop a method for detecting an antigen for solving the problems, and as a result, the method of the present invention has been designed.

A method for measuring an antigen in an analysis sample according to the method of the present invention will be described in detail as follows.

Step (a): Contact of Analysis Sample with Detection Antibody

First, an analysis sample is contacted with a detection antibody with which a marker generating a detectable signal is combined and which specifically binds to the antigen.

The samples includes organic materials derived from mammals and synthetic organic molecules, but not limited to. Examples of the samples include whole blood, serum, plasma, body fluid or cell culture supernatant.

The term "organic molecules" refers to molecules that have covalent bonds between carbon, nitrogen, oxygen and/or sulfur atom. The organic molecules may be selected from small-sized molecules such carbon monoxide to complex large-sized molecules such as polymer, or the organic molecules may be glycoside molecules.

The term "antigens" as used herein, refers to any molecule that can be detected using a method of the present invention. The term includes, for example, small molecules in body fluid such as drugs, toxins, autoantibodies, autoantigens, proteins, carbohydrates, nucleic acids and other molecules. Examples of antigens potential present in the serum of a subject include, but are not limited to drugs, such as barbotirate, tricyclic antidepressants (TCA), Digitalis, tumor antigen (e.g. antigens associated with breast, testis, brain, liver, large intestine, pancreas, stomach or lung), virus antigens (e.g. antigens associated with HIV, influenza or other viruses), bacterial antigens (e.g. in systemic bacterial infections), hormones (e.g. thyroid stimulating hormone (TSH), human growth hormones, progesterone, testosterone, human chorionic gonadotrophin (hCG)), plasma proteins (e.g., a fibrin degradation product (FDP), a C-reactive protein (CRP), a carcinoembryonic protein, α-fetoprotein (AFP), carcinoembryonic antigen (CEA)), protozoal antigens, plaque antigens, haptens (e.g., angiotensin I, vasopressin, somatostatin, atrial natriuretic hormone, endoserine, luteinizing hormone releasing hormone (LHRH), kassinin or other peptides), steroids (e.g., cortisol), and cytokines such as interleukin-1, interferon-α, interferon-β, interferon-γ, interleukin-2, interleukin-4, interleukin-6, interleukin-7, interleukin-12, interleukin-15, B7, CD28, or other members of the Ig superfamily.

The virus antigens include, for example, antigens associated with or produced by hepatitis type A, hepatitis type B, hepatitis type C, influenza, varicella, adenovirus, herpes simplex type I (HSV-I), herpes simplex type II (HSV-II), rinderpest, rhinovirus, echovirus, rotavirus, respiratory syncytial virus, papilloma virus, papova virus, cytomegalovirus, echinovirus, arbovirus, hantavirus, coxsachie virus, mumps virus, measles virus, rubella virus, polio virus, human immunodeficiency virus type I (HIV-I), and human immunodeficiency virus type II (HIV-II), any picornaviridae, enteroviruses, togaviruses, such as alphaviruses, flaviviruses, coronaviruses, rabies virus, ebola viruses, human T cell leukemia virus type I, human T cell leukemia virus type II, lentiviruses, polyomaviruses, parvoviruses, Epstein-Barr virus, human herpesvirus-6, cercopithecine herpes virus 1 (B virus) and poxviruses, but not limited to.

The bacterial antigens include, for example, antigens associated with or produced by *Mycobacteria rickettsia, Mycoplasma, Neisseria* spp. (e.g., *Neisseria menigitidis* and *Neisseria gonorrhoeae*), *Legionella, Vibrio cholerae*, Streptococci, such as *Streptococcus pneumoniae, Corynebacteria diphtheriae, Clostridium tetani, Bordetella pertussis, Haemophilus* spp. (e.g., *influenzae*), *Chlamydia* spp., and enterotoxigenic *Escherichia coli*, but not limited to.

Protozoal antigens include, for example, antigens associated with or produced by plasmodia, *eimeria, Leishmania*, and *trypanosoma*. Additional antigens include pollutants, toxins, noxious chemicals, forensic material and the like, but not limited to.

The tumor-related antigens include, for example, antigens associated with survivin, cyclin D1, Her2/neu, K-ras, chymotrypsinogen, XIAP (X-linked inhibitor of apoptosis protein), basic fibroblast growth factor (bFGF), Epidermal Growth Factor receptor, carcinoembryonic antigen (CEA), prostate-specific antigen (PSA), α-fetoprotein, β-2-microglobulin, bladder tumor antigen (BTA), chromogranin A, neuron-specific enolase, S-100 protein, TA-90 protein, tissue peptide antigen (TPA) and human chorionic gonadotropin (hCG), but not limited to. Preferably, the tumor-related antigen is prostate-specific antigen.

The antigens also include contaminants, toxins, poisonous chemicals, medicolegal materials or similar materials thereof.

According to a preferred embodiment, the antigens are drugs, toxins, autoantibodies, autoantigens, proteins, carbohydrates, nucleic acids or tumor related antigen. More preferably, the antigen is tumor-related antigen.

The method of the present invention employs two types of antibodies, that is, a detection antibody and a capture antibody. The term "detection antibody" refers to an antibody that can bind to the antigen captured by the capture antibody or a reference substance. The term "capture antibody" herein refers to an antibody that can bind to the antibody to be detected in the analysis sample. The antibody that can be used in the method of the present invention is for detecting an antigen in an analysis sample, and includes an epitope having a nucleotide sequence specifically binding to the antigen in the analysis sample. The antibody of this invention includes epitope, antigen, the entire antibody capable of binding to antigen fragment and antibody fragment (e.g. F(ab') 2, Fab', Fab, Fv). The antibody of this invention includes, but not limited to, monoclonal antibody or polyclonal antibody, preferably, the antibody is monoclonal antibody.

The antibody of this invention may be manufactured by various methods known to those skilled in the art and its practical method is described in Fusion Methods (Kohler and Milstein, European Journal of Immunology, 6:511-519 (1976)), recombinant DNA method (U.S. Pat. No. 481,656) or phage antibody library method (Clackson et al, Nature, 352:624-628(1991) and Marks et al, J. Mol. Biol., 222:58, 1-597(1991)). The procedures for manufacturing antibodies is describe in Harlow, E. and Lane, D., Using Antibodies: A Laboratory Manual, Cold Spring Harbor Press, New York, 1999; Zola, H., Monoclonal Antibodies: A Manual of Techniques, CRC Press, Inc., Boca Raton, Fla., 1984; and Coligan, CURRENT PROTOCOLS IN IMMUNOLOGY, Wiley/Greene, N.Y., 1991, these documents are entirely incorporated by reference into the present specification A marker generating a detectable signal is combined with the detection antibody. The term "signal" refers to a detectable parameter, and includes the flow of optical, electric, or magnetic parameters, fluorescence emission, infrared radiation, ultraviolet radiation, chemiluminescence, light reflection, and the absorption degree of the signal. The marker generating a detectable signal includes chemicals (e.g. biotin), enzymes (alkaline phosphatase, β-galactosidase, horse radish peroxidase and cytochrome P450), radioactive matter (e.g. 14C, 125I, 3H, 32P and 35S), fluorescence substance (e.g. fluoresin), luminous substance, chemiluminescent and FRET (fluorescence resonance energy transfer), but not limited to. The various label and the labeling method are described in Ed Harlow and David Lane, Using Antibodies:A Laboratory Manual, Cold Spring Harbor Laboratory Press, 1999. Preferably, the marker generating a detectable signal is fluorescence substance.

The marker can be detected to different fluorescent signals depending on the emitting wavelength, preferably, the marker combined with the detection antibody binds to the capture antibody or the reference substance. The marker includes fluorescein and its derivatives, rhodamine and its derivatives, lucifer yellow, B-phytoerythrin, 9-acrydine isothiocyanate, lucifer yellow VS, 4-acetamido-4'-isothiocyanatostilbene-2,2'-disulfonate, 7-diethylamino-3-(4'-isothiocyatophenyl)–4-methylcoumarin, succinimidyl-pyrenebutyrate, 4-acetoamido-4'-isothiocyanatostilbene-2,2'-disulfonate derivatives, LC™-Red 640, LC™-Red 705, PC5, Cy5, Cy5.5, resamine, isothiocyanate, erythrosine isothiocyanate, diethyltriamine pentaacetate, 1-dimethylaminonaphthyl-5-sulfonate, 1-anilino-8-naphthalenesulfonate, 2-p-toluidinyl-6-naphthalenesulfonate, 3-phenyl-7-isocyanatocoumarin, 9-isothiocyanatoacridine, acridine orange, N-(p-(2-benzoxazolyl)phenyl)meleimide, benzoxadiazol, stilbene and pyrene, but not limited to.

According to the method of the present invention, the signal released by the marker combined with an antigen-specific detection antibody is measured as a fluorescent signal, and thus the presence or absence and amount of antigen to be detected can be confirmed by measuring both signals of the test zone and the reference zone, respectively. The detection antibody and the capture antibody have such affinity as to specifically bind to the antigen, and do not react with any other reagent used in the method of the present invention.

Step (b): Contact of Capture Antibody with Resultant Product of Step (a)

Then, a capture antibody which specifically binds to an antigen to be detected is contacted with the resultant product of step (a). That is, the resultant product of step (a) is bound to an antigen-specific capture antibody or a reference substance of a test zone or a reference zone.

Herein, the term "capture antibody" is the same as described in step (a).

According to a preferable embodiment of the present invention, the capture antibody is bound to a surface of a solid substrate, and the capture antibody is present on a surface of a substrate of one reaction container in which the reactant continuously flows. The reaction container is a microchip having a microchannel.

The term "solid substrate" refers to a non-liquid materiel, is used herein to mean the same as a solid support or solid phase. The solid substrate can be formed in microchannels, for example, membrane, a part of capillary tube, or as a small diameter beads floating/attaching in microchannels. This type of materials include polystyrene and polypropylene, glass, metal and hydrocarbon polymers such as gel. The solid substrate can be as dipstick, microtiter plate, particles (e.g. bead), affinity column and immunoblot membrane (e.g. polyvinylidene fluoride membrane (U.S. Pat. No. 5,143,825, U.S. Pat. No. 5,374,530, U.S. Pat. No. 4,908,305 and U.S. Pat. No. 5,498,551).

According to another preferable embodiment of the present invention, the microchannel of the microchip includes a test zone and a reference zone. The capture antibody is bound to a surface of the test zone, and the reference substance is bound to the reference zone.

As used herein, the term "test zone" refers to a section which is included in the microchannel of the microchip. The capture antibody is bound to a surface of the test zone, and the antigen to be detected and a detection antibody which specifically binds to the antigen bind to the capture antibody.

As used herein, the term "reference zone" refers to a section which is included in the microchannel of the microchip. The reference substance is bound to a surface of the reference zone, and a detection antibody which specifically binds to the antigen bind to the reference substance.

As used herein, the term "reference substance" refers to a substance to which the detection antibody can bind. According to a preferable embodiment of the present invention, the reference substance includes the same material as the antigen or a fragment of the antigen including the epitope.

The antibodies, antigens or reference substances can be attached to solid phase material by physical adsorption or chemical attaching. Physical adsorption is performed by reaction between the solid phase material and antigen or antibody in a suitable buffer solution. As the buffer solution, phosphate buffer solution, tris-hydrochloride buffer solution, carbonate buffer solution, etc. The reaction is achieved by mixing and holding them for a certain time at 4° C. to 37° C., preferably at room temperature. The chemical attaching may be performed by using carbodiimide method among peptide attaching method. Another chemical method is a method performed in divalent cross-linking reagent such as glutaraldehyde or cyanutric chloride (cf. "Peptide Synthetic Method", Maruzen, 1975 or "Enzyme Immunoassay Method", Kyoritsu Shuppan, "Protein Nucleic acid Enzyme", special issue No. 31, 1987).

According to a preferable embodiment of the present invention, the analysis sample is applied to the microchip, and the applied analysis sample is contacted with the test zone and the reference zone through the flow that is formed in the microchannel. In addition, the analysis sample may be sequentially contacted with the test zone and the reference zone or may be sequentially contacted with the reference zone and the test zone.

As described above, the detection of the present invention is described such that the analysis sample is contacted with the detection antibody and then the capture antibody is contacted with the resultant product. However, this is only for convenience of description, and thus the detection method of the present invention does not exclude i) a case contrary to the above procedure, that is, preferentially performing a step of contacting the analysis sample with the capture antibody, and then performing a step of contacting the detection antibody with the reaction resultant product of the analysis sample and the capture antibody; and ii) simultaneously contacting the analysis sample with the capture antibody and the capture antibody.

In the above procedure, when the step of contacting the analysis sample with the detection antibody is preferentially performed, and then the step of contacting the capture antibody with the reaction resultant product of the analysis sample and the detection antibody is performed, the reaction of the analysis sample and the detection antibody may be made inside or outside the microchip. According to a specific embodiment of the present invention, the reaction may be made outside the microchip.

Step (c): Contact of Reference Substance with Detection Antibody to which Marker Generating Detectable Signal is Combined After the contact of the detection antibody with the resultant product of step (a), a reference substance which is bound to a surface of a solid substrate and includes an epitope to which the detection antibody specifically binds is contacted with the detection antibody with which the marker generating a detectable signal is combined.

As used herein, the term "epitope" refers to a part of an antigen to which an antibody binds, that is, an antigenic determinant. The reference substance may include at least one kind of epitope, or may include one or more identical epitopes. However, the epitope to which the detection antibody binds preferably has a sequence which can be found only once on the reference substance.

Step (d): Signal Measurement

Then, the signals generated from the markers of the resultant product of step (b) and the resultant product of step (c) were measured using a signal measurement apparatus. Detailed descriptions of the signal measurement apparatus are set forth as below.

Step (e): Signal Analysis

The signal measured in step (d) is analyzed to determine the presence or absence and amount of antigen in the analysis sample.

The presence or absence and amount of antigen are determined according to the amount of signal. The term "amount" refers to the degree to which the intensity of the signal as a physical parameter is increased, decreased, or maintained, based on the premise that the sensitivity of the signal is included within a certain measurable level. For example, the amount of signal can be measured if the intensity of the signal increases by a unit of 10 and the measurement sensitivity of the signal is of a unit of 1. The amount of the signal may be expressed as a predetermined unit.

Here, steps (a) to (d) or steps (b) to (d) may be performed on a microchip having a microchannel, and the analyzing of the signal may be performed by measuring signals of a reaction start zone, a test zone, a reference zone, and a reaction end zone.

The error rate (%) may be calculated from the signals of the reaction start zone and the reaction end zone. When the error rate is 20% or higher, the analyzing is again performed to improve reliability of the signals of the test zone and the reference zone. The signal analysis results may vary due to non-uniform viscosity or fluidity of an analysis sample, or the signal analysis results may vary due to crude manipulation of experimenters who conduct analysis. The term "error rate" refers to a value which is measured in order to minimize errors occurring therefrom, and obtain reliability of data.

The terms "reaction start zone" and "reaction end zone" refer to sections included in the microchannel of the microchip, and correspond to some of sections (0-900) obtained by dividing a signal measurement area in the microchannel into predetermined intervals.

The sections for the reaction start zone and the reaction end zone may vary depending on the kind of antigen. For example, in the case of an experiment of detecting a PSA antigen using the method of the present invention, the reaction start zone corresponds to sections 180 to 370 and the reaction end zone corresponds to sections 700 to 880 in the entire of sections "0 to 900" (see, FIG. 1).

The signal measurement area in the microchannel is composed of the reaction start zone, the test zone, the reference zone, and the reaction end zone. When the signals of the respective zones are shown as a graph, the amount of signals is calculated as follows. On the graph, the horizontal axis may be marked as sections (0-900) obtained by dividing the signal measurement area in the microchannel into predetermined intervals, and the vertical axis may be marked as the amount (intensity) of a fluorescent signal.

$$\text{Fluorescent signal of test zone} = \int_{X_{tc}-30}^{X_{tc}+30}(X_n - X_b) \quad [\text{Equation 1}]$$

$$\text{Fluorescent signal of reference zone} = \int_{X_{rc}-30}^{X_{rc}+30}(X_n - X_b) \quad [\text{Equation 2}]$$

(Xn=Fluorescent signal at point n
Xtc=Fluorescent signal at center point of test zone
Xrc=Fluorescent signal at center point of reference zone
Xb=Average value of fluorescent signals of at least 50 points among point 0 to point 900 of the microchannel)

$$\text{Fluorescent signal of reaction start zone} = (\Sigma_{X_{tc}-(X_{rc}-X_{tc})-30}^{X_{tc}-(X_{rc}-X_{tc})+30} X_n)/60 \quad [\text{Equation 3}]$$

$$\text{Fluorescent signal of reaction end zone} = (\Sigma_{X_{rc}+(X_{rc}-X_{tc})-30}^{X_{rc}+(X_{rc}-X_{tc})+30} X_n)/60 \quad [\text{Equation 4}]$$

(Xn=Fluorescent signal at point n
Xtc=Fluorescent signal at center point of test zone
Xrc=Fluorescent signal at center point of reference zone)

That is, the fluorescent signal of the reaction start zone is an average value of signals of respective points from point Xtc−(Xrc−Xtc)−30 to point Xtc−(Xrc−Xtc)+30, and the fluorescent signal of the reaction end zone is an average value of signals of respective points from point Xrc+(Xrc−Xtc)−30 to point Xrc+(Xrc−Xtc)+30.

The error rate may be calculated as follows.

$$\text{Error rate (\%)} = [|(\text{signal of reaction start zone} - \text{signal of reaction end zone})|/\text{signal of reaction start zone}] \times 100 \quad [\text{Equation 5}]$$

According to a preferable embodiment of the present invention, the measured signal is analyzed by calculating the ratio value of intensities of signals generated from markers of the resultant product of step (b) and the resultant product of step (c).

According to the conventional method for detecting an antigen, a substance specifically binding to the antigen to be detected (the capture antibody in the present invention) was bound to the test zone, a foreign substance to which a human-derived antigen cannot bind was bound to the reference zone, and signals generated from the respective zones were measured. The signal of the reference zone was used as a numerical value for correcting the signal of the test zone. Although samples have the same concentration, the flow rates (reaction rates) of the samples flowing in the microchannel are different from each other due to a difference in viscosity between the samples, resulting in different signals in the test zone. In order to correct this, the lower-viscosity sample with the same concentration is allowed to pass quickly through the microchannel, thereby reducing the signal of the test zone and thus reducing the signal of the reference zone together, and the higher-viscosity sample with the same concentration is allowed to slowly pass through the microchannel, thereby increasing the signal of the test zone and thus increasing the signal of the reference zone together, so that the samples exhibit the same ratio value regardless of the difference in viscosity therebetween, resulting in substantially the same ratio value regardless of different signal values. The term "substantially" refers to the inclusion of a case where it is not influenced by the difference in viscosity between the samples, or a case where, although it is influenced by the difference in viscosity between the samples, the degree of influence is slight and thus it may not be influenced by the difference in viscosity between the samples. For example, the ratio value of signal intensity between the test zone and the reference zone is almost kept constant with a deviation of ±2.0 despite the difference in viscosity between the samples. This means that the ratio value of signal intensity is not substantially influenced by the difference in viscosity between the samples.

However, the above method had problems in that, when the analysis sample is for example human blood plasma, i) since a reference substance bound to a reference zone cannot be a human derived peptide or a substance bindable therewith, there is a limit to selecting the reference substance; ii) since different detection antibodies are bound to the test zone and the reference zone, the detection result may vary depending on the affinity to each antibody to antigen; iii) since, in the case of a high concentration of analysis sample, the detection antibody of the reference zone continuously binds to the reference zone at a uniform level regardless of the saturation degree of the detection antibody bound to the test zone, the ratio value of intensity of the measurement signal of the test zone/the signal of the reference zone is not constant; and iv) since the antigen-antibody reaction is basically used, the effect by the temperature, which is incidentally problematic, cannot be ruled out. Therefore, the present inventors have developed the method of the present invention capable of improving stability, reliability, and reproducibility of data by minimizing influences due to a limit in selecting the reference substance and the concentration and temperature of the analysis sample. Here, one of the most distinguished characteristics of the present invention is that the influences by the concentration and temperature of the analysis sample were minimized with respect to the detection of an antigen in the analysis sample.

According to another preferable embodiment of the present invention, the ratio value of intensities of signals generated from the markers of the resultant product of step (b) and the resultant product of step (c) is linearly proportional to the concentration of the analysis sample of step (a).

According to another preferable embodiment of the present invention, the ratio value of intensities of signals generated from the markers of the resultant product of step (b) and the resultant product of step (c) is not substantially influenced by a change in temperature at which the method is conducted. The term "substantially" refers to the inclusion of a case where it is not influenced by the difference in temperature, or a case where, although it is influenced by the difference in temperature, the degree of influence is slight and thus it may not be influenced by the difference in temperature. For example, the ratio value of signal intensity between the test zone and the reference zone is almost kept constant with a deviation of ±0.17 despite the difference in temperature. This means that the ratio value of signal intensity is not substantially influenced by the difference in temperature.

According to another preferable embodiment of the present invention, the ratio value of intensities of the signals generated from the markers of the resultant product of step (b) and the resultant product of step (c) shows the same value at a temperature range of 10-30° C. at which the method is conducted.

The method of the present invention enables quantitative detection of antigen even in a sample containing a high-concentration antigen, for example, when the concentration of antigen is 1800 ng/ml or more. According to one example, when the method of the present invention is employed to detect a PSA antigen, the concentration of PSA antigen can be obtained from the experimentally measured T/R ratio graph in the case of a sample having a PSA concentration of 0.0001-1500 ng/ml, and obtained from an extension of the experimentally obtained graph in the case of a sample having a PSA concentration of 1500-1800 ng/ml and 1800 ng/ml or more. According to another example, the method of the present invention enables the measurement and detection of a high-concentration specimen containing a PSA concentration of 4000 ng/mL or more. That is, the concentration of PSA antigen can be obtained from the experimentally measured T/R ratio graph in the case of a sample having a PSA concentration of 0.0001-4500 ng/ml, and obtained from an extension of the experimentally obtained graph in the case of a sample having a PSA concentration of 4500 ng/ml or more.

According to another aspect of the present invention, there is provided an apparatus for detecting an antigen in an analysis sample, the apparatus including:

(a) a microchip having a microchannel in which the analysis sample is accommodated and a reaction occurs;

(b) a test zone formed at a portion of the microchannel and having a surface to which a capture antibody is bound, the capture antibody specifically binding to an antigen to be detected; and (c) a reference zone formed at a portion of the microchannel and having a surface to which a reference substance is bound, the reference substance including an epitope to which a detection antibody specifically binds.

The apparatus for detecting an antigen using the method of the present invention is not influenced by affinity of the antigen, the concentration of the analysis sample, and the detection temperature, thereby accurately measuring the amount of antigen to be detected, and is easily operated even without specialized skills, thereby allowing on-site diagnosis in detecting a target antigen. The apparatus for detecting an antigen of the present invention is for the foregoing method for detecting an antigen of the present invention, and descriptions of overlapping contents therebetween are omitted to avoid excessive complication of the specification due to repetitive descriptions thereof.

Respective components of the apparatus of the present invention will be described in detail.

Component (a): Microchip Having Microchannel

The apparatus for detecting an antigen includes a microchip in which the analysis sample is accommodated and a reaction occurs. The microchip includes a microchannel for accommodating the analysis sample therein, and the microchannel may have various depths.

The microchip which can accommodate the analysis sample may include at least one microchannel, and a capture antibody and a reference substance for respectively detecting different antigens may be bound to the microchannel. The microchannel includes a reaction start zone, a test zone, a reference zone, and a reaction end zone, and the respective zones are preferably located in the order of the reaction start zone, the test zone, the reference zone, and the reaction end zone.

The detection apparatus using the foregoing method of the present invention is described such that the reactions of the analysis sample with the capture antibody and the detection antibody, the reaction of the reference substance and the detection antibody, and the like are performed for respective steps, but this is only for convenience of description, and thus the apparatus for detecting an antigen of the present invention can measure the presence or absence and amount of antigen only by dispensing the analysis sample in the microchip. Therefore, the microchip preferably includes i) the reagent, the reference substance, and the capture antibody, or ii) the reagent, the reference substance, and the detection antibody with which a signal generating marker is combined, and the capture antibody, of which all are used in the method for detecting an antigen. The microchip is manufactured such that, when the analysis sample is dropped in the microchannel and the microchip is mounted on the apparatus according to the present invention, the presence or absence and amount of antigen can be automatically measured. Therefore, the apparatus of the present invention is easy to use and is also suitable for on-site diagnosis, and thus can be easily used by the general public as well as professionals.

The microchannel may include an inlet into which the analysis sample is injected. When the analysis sample flows into the microchannel through the inlet, the analysis sample may react with a reaction agent while passing through the microchannel, to detect an antigen to be detected or measure the amount of antigen.

According to a specific embodiment of the present invention, a labeling reaction of the analysis sample using a fluorescent material, a specific reaction of the analysis sample using an antigen-antibody reaction, and the like may occur in the microchannel to detect an antigen to be detected. That is, a protein antigen-antibody specific reaction or the like is used, thereby selectively confirming only a desired antigen later through various detection units such as a sensor. The labeled analysis sample passes through the microchannel, and here, one sectional surface of the microchannel is exposed to an optical sensor, which is then used to detect a fluorescence signal.

Component (b): Test Zone

As for the apparatus for detecting an antigen of the present invention, the test zone is formed at a portion of the microchannel, and designed such that the capture antibody specifically binding to the antigen is bound to a surface of the test zone.

Component (c): Reference Zone

As for the apparatus for detecting an antigen of the present invention, the reference zone is formed at a portion of the microchannel, and designed such that the reference substance is bound to a surface of the reference zone, the reference substance including an epitope to which the detection antibody specifically binds.

According to a preferable embodiment of the present invention, the apparatus may further include a detection antibody with which a marker generating a detectable signal is combined and which specifically binds to the antigen.

According to another preferable embodiment of the present invention, the apparatus may further include a measurement unit for measuring a signal generated from the marker, or the apparatus may further include an analysis unit for calculating the ratio value of intensities of the signals measured in the test zone and the reference zone.

The measurement unit refers to a component of the apparatus, through which the signal generated from the marker combined with the detection antibody passes, and includes for example an optical component. The measurement unit passes the fluorescence signal therethrough and then transmits the fluorescence signal to the signal analysis unit, and may partially convert the fluorescence signal into an electric signal. The measurement unit may be provided integrally with the apparatus according to the present invention or may be provided as an independent device.

The analysis unit may be used in the same meaning as a signal processor, and refers to a component of the apparatus, which may partially change the signals measured in the test zone and the reference zone or may correct the measurement values of the signals. The analysis unit may simultaneously operate with the optical component, and may convert the fluorescence signal into an electric signal.

The method and the apparatus of the present invention may be used in various manners. For example, in the case where a prostate cancer-related antigen is detected, the prostate specific antigen (PSA) is used as a tumor marker, thereby allowing clinical determination on the presence or absence of benign and malignant prostate cancer cells, and the reoccurrence or not, degree of risk, and spread of prostate cancer, and promptly reporting the disease progression. Further, the method of the present invention can be used in the efficacy evaluation of drugs used to treat the prostate cancer.

Advantageous Effects

Features and advantages of the present invention are summarized as follows:

(a) The present invention is directed to a novel method for detecting an antigen and an apparatus for detecting an antigen using the same.

(b) Unlike the conventional method in which substances having different epitopes are bound to the test zone and the reference zone to detect an antigen specifically binding to the test zone, the method for detecting an antigen of the present invention enables a more accurate detection of the presence or absence and amount of antigen by binding a reference substance including the same epitope as an antigen to be detected to the reference zone.

(c) The conventional method for detecting an antigen has disadvantages in that the reactivity decreases as the concentration of antigen is higher, and the signal value no longer increases at a predetermined level when the reaction is saturated. However, the method for detecting an antigen of the present invention does not cause this hook effect, thereby resultantly increasing the detection range, by measuring the test value from the T/R ratio value.

(d) Further, the method for detecting an antigen of the present invention can control the flow of an analysis sample and the reaction time, thereby improving sensitivity and minimizing the influences by the concentration of the analysis sample or the temperature of the detection reaction, and thus improving stability, reliability, and reproducibility of data, when compared with the conventional method for detecting an antigen.

(e) Accordingly, the method and apparatus for detecting an antigen of the present invention can be easily operated without specialized skills, thereby instantly obtaining the presence or absence and amount of detection antigen in the analysis sample through on-site diagnosis.

MODE FOR CARRYING OUT THE INVENTION

Figure 1:
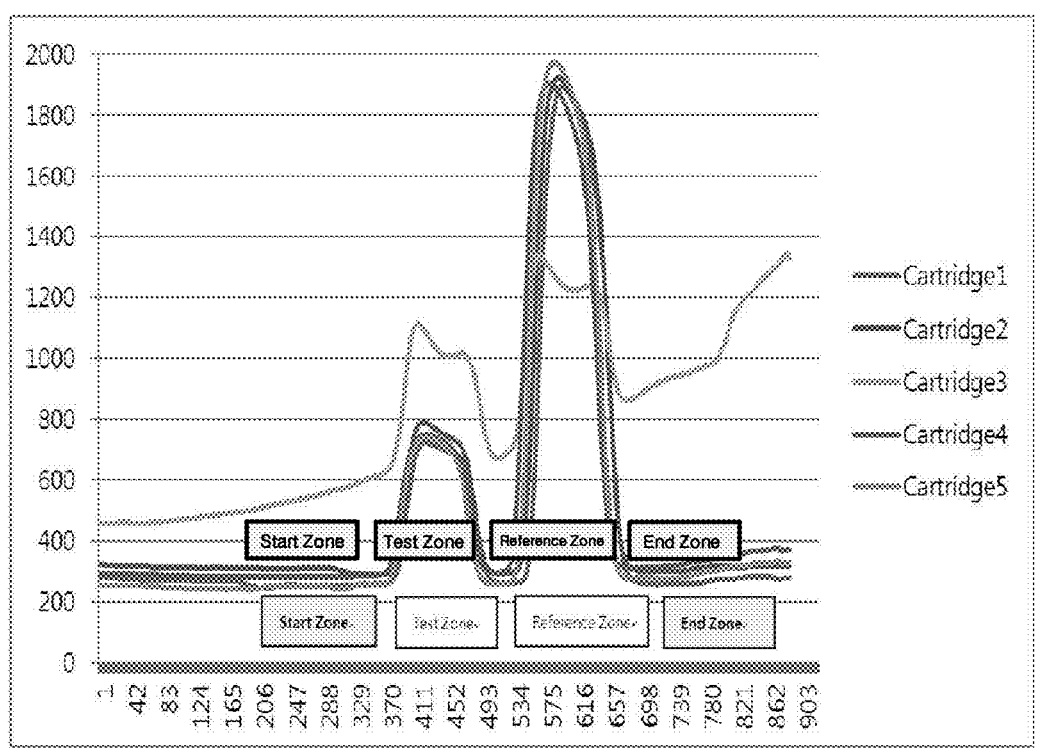
FIG. 1 shows signal measurement results for five cartridges in order to test the validity of a signal measurement value measured by a method for detecting an antigen of the present invention. The horizontal axis is marked as sections obtained by dividing a signal measurement area in the microchannel into predetermined intervals, and the vertical axis is marked as the intensity value of a fluorescent signal.

The present invention will now be described in further detail by examples. It would be obvious to those skilled in the art that these examples are intended to be more concretely illustrative and the scope of the present invention as set forth in the appended claims is not limited to or by the examples.

EXAMPLES

Example 1: Measurement of Detection Data by Correction of Flow Rate 1-1. PSA Detection Using Method for Detecting Antigen of Present Invention The blood samples used herein were obtained from patients who requested examinations at an outpatient laboratory of the Department of Laboratory Medicine, Korea University Ansan Hospital, and the patient groups were randomly selected.

The amount of antigen in the patient samples was measured using an apparatus for detecting an antigen using the method of the present invention. The patient groups are prostate cancer patients, and the amount of PSA present in the patient serum was measured by using prostatic specific antigen (PSA) as a tumor marker.

Prostate specific antigen (PSA) is a single chain 33 kDa glycoprotein that is produced almost mainly by the human prostate epithelium and present at levels of 0.5 to 2.0 mg/ml in human seminal fluid. The prostatic specific antigen is proteinase synthesized in prostate epithelium cells, and is a useful tumor marker used to select prostate cancer since the prostatic specific antigen is hardly expressed in tissues other than prostate tissues. The prostatic specific antigen is specific to prostate tissues but not specific to tumors. Therefore, the prostatic specific antigen may also increase in benign prostatic hyperplasia, prostatitis, prostatic infarct, and the like, and is useful in determining a reoccurrence after surgery as well as selectively testing prostate cancer.

Of the blood samples obtained from the patient groups, samples with the same concentration but different viscosities were selected, and the measurement of antigen was conducted using the apparatus for detecting an antigen using the present invention. 30 μl of a sample (patient serum or plasma with or without lipoprotein lipase) was dropped around the sample inlet of a chip (or cartridge). Five minutes after the sample was dropped, the chip was inserted into the apparatus for detecting an antigen according to the present invention. After about 40 seconds, the degree of presence of prostate specific antigen in the sample was quantitatively displayed on a display screen, and signal intensity values of a test zone and a reference zone were also displayed.

Signal values for patient A and patient B were respectively measured, and these measurement values were used to calculate the ratio values of signal intensity of test zone (T)/reference zone (R) (Table 1). The method for calculating signals of the respective zones was shown using equation 1 and equation 2.

$$\text{Fluorescent signal of test zone} = \int_{Xtc-30}^{Xtc+30}(Xn-Xb) \quad \text{[Equation 1]}$$

$$\text{Fluorescent signal of reference zone} = \int_{Xrc-30}^{Xrc+30}(Xn-Xb) \quad \text{[Equation 2]}$$

$Xn$=Fluorescent signal at point n
$Xtc$=Fluorescent signal at center point of test zone
$Xrc$=Fluorescent signal at center point of reference zone
$Xb$=average value of fluorescent signals of at least 50 points among point 0 to point 900 of the microchannel, and 0-900 means sections obtained by dividing the signal measurement area in the microchannel into predetermined intervals.

TABLE 1

Signal intensities of respective zones and ratio values thereof

| Patient groups | Signal intensity of test zone (T) | Signal intensity of reference zone (R) | Ratio (T/R) |
|---|---|---|---|
| Patient A | 500 | 500 | 1.0 |
| Patient B | 1000 | 1000 | 1.0 |

As a result, through comparison of only the signal intensity, the signal intensity of patient B was higher, but as a result of calculation of the ratio value of signal intensity between the test zone and the reference zone, the amounts of prostate specific antigen in the samples for both patients were analyzed to be the same.

Together with the results of Table 1 above, the standard deviation (CV, %) that may be generated in the ratio value of signal intensity between the test zone and the reference zone was calculated (Table 2). Here, one of the analysis samples was selected, and the same analysis sample was dispensed into five cartridges, and then subjected to the following analysis.

TABLE 2

| — | Signal intensity of test zone (T) | Signal intensity of Reference zone (R) | Ratio (T/R) |
|---|---|---|---|
| Cartridge 1 | 21302 | 74288 | 3.487 |
| Cartridge 2 | 24603 | 84160 | 3.421 |
| Cartridge 3 | 26133 | 93322 | 3.571 |
| Cartridge 4 | 30427 | 104619 | 3.438 |
| Cartridge 5 | 32557 | 112542 | 3.457 |
| Standard deviation | 16.72 | 16.36 | 1.70 |

As a result, the signal intensities of the test zone and the reference zone are slightly different for respective analysis cartridges, but the ratio values of signal intensity of test zone/reference zone (T/R) were showed to be almost constant.

1-2. Establishment of Conditions of Method for Detecting Antigen of Present Invention The purpose of the method for detecting an antigen of the present invention is that the flow of the analysis sample is controlled and the reaction time is controlled, thereby removing disadvantages that may be shown in a flow reaction and thus improving the reaction sensitivity as much as possible. Therefore, experiments associated with achievement of this purpose were conducted. That is, the error rate analysis was conducted in order to test the validity of the signal measurement value measured by the method for detecting an antigen of the present invention, and the error rate was calculated by equations 3 to 5. The fluorescent signal of the reaction start zone is an average value of signals of respective points from point Xtc−(Xrc−Xtc)−30 to point Xtc−(Xrc−Xtc)+30, and the fluorescent signal of the reaction end zone is an average value of signals of respective points from point Xrc+(Xrc−Xtc)−30 to point Xrc+(Xrc−Xtc)+30.

Fluorescent signal of reaction start zone=
$(\Sigma_{Xtc-(Xrc-Xtc)-30}^{Xtc-(Xrc-Xtc)+30} Xn)/60$ [Equation 3]

Fluorescent signal of reaction end zone=
$(\Sigma_{Xrc+(Xrc-Xtc)-30}^{Xrc+(Xrc-Xtc)+30} Xn)/60$ [Equation 4]

$Xn$=Fluorescent signal at point n
$Xtc$=Fluorescent signal at center point of test zone
$Xrc$=Fluorescent signal at center point of reference zone Error rate (%)=[|(signal of reaction start zone−signal of reaction end zone|/signal of reaction start zone]×100 [Equation 5]

In the microchips, that is, cartridges 1 to 5, into which respective samples are injected, signals of the reaction start zone and the reaction end zone were measured, and the error rate was calculated from the reaction start zone and the reaction end zone (see, Table 3 and FIG. 1).

TABLE 3

Error rate measurement

| — | Signal of reaction start zone | Signal of reaction end zone | Error rate (%) | Display unit of measurement unit |
|---|---|---|---|---|
| Cartridge 1 | 252 | 263 | 4.34 | Normal |
| Cartridge 2 | 309 | 308 | 0.46 | Normal |
| Cartridge 3 | 530 | 960 | 81.23 | Inadequacy |
| Cartridge 4 | 282 | 329 | 16.68 | Normal |
| Cartridge 5 | 250 | 288 | 15.47 | Normal |

As a result, it was measured that the error rate was the highest in the analysis sample of cartridge 3. When the error rate was 20% or higher, the analysis was again conducted after the concentration of the analysis sample was controlled.

Example 2: Comparison of Detection Data According to Concentration of Analysis Sample A comparison test on the resolution of measurement result values when an analysis sample has a high concentration was conducted using the detection method of the present invention and the conventional detection method (Rabbit IgG reference system).

2-1. PSA Detection Using Conventional Method for Detecting Antigen

For a reference value for prostate specific antigen detection results according to the method of the present invention, a prostate specific antigen detection experiment was conducted as follows.

Among the samples used in the present invention, a patient sample having a high concentration on a non-linear section was selected, and the measurement was conducted using the apparatus for detecting an antigen using the present invention. 30 μl of a sample (patient serum or plasma with or without lipoprotein lipase) was dropped around the sample inlet of a chip. Five minutes after the sample was dropped, the chip was inserted into the apparatus for detecting an antigen according the present invention. After about 40 seconds, the degree of presence of prostate specific antigen in the sample was quantitatively displayed on the display screen, and the signal intensity values of the test zone and the reference zone were also displayed.

Figure 2A:
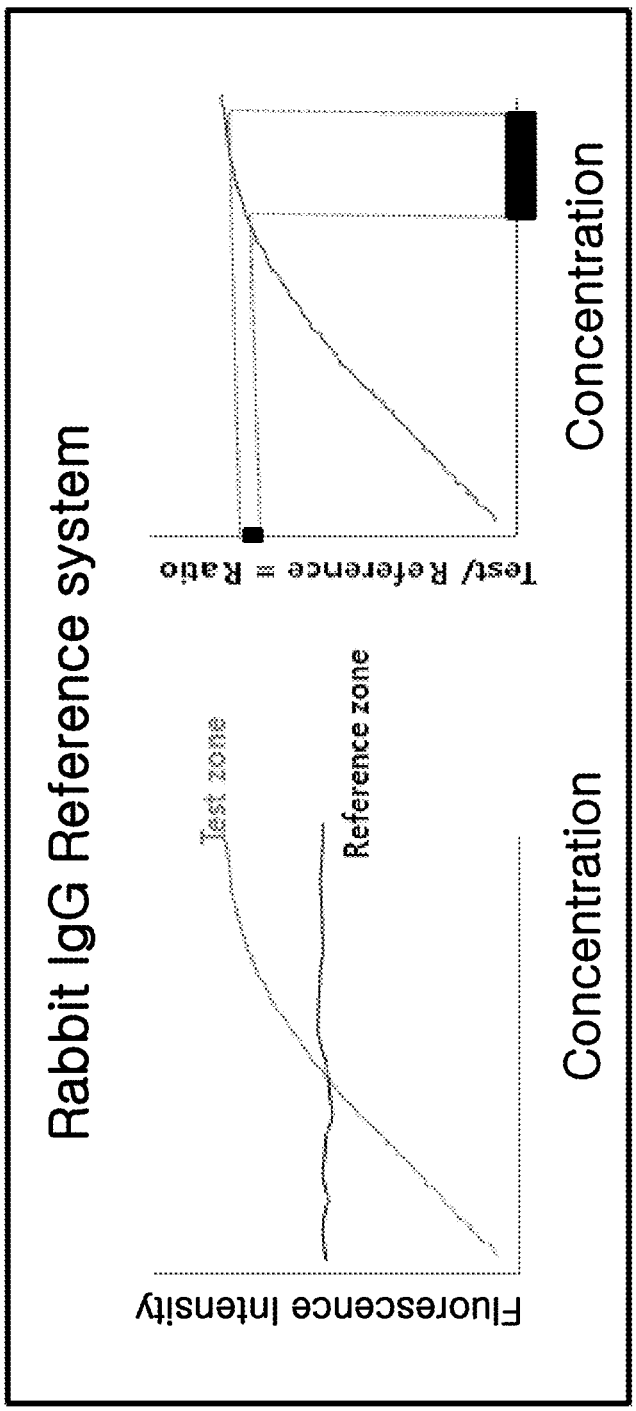
FIG. 2a are graphs respectively showing (i) signal intensities of a test zone and a reference zone according to the concentration of an analysis sample and (ii) a ratio value of signal intensity of test zone/reference zone according to the concentration of the analysis sample, using a Rabbit IgG reference system, which is the conventional method for detecting an antigen.

As a result, it could be confirmed that, as the concentration of the analysis sample becomes higher, the increase in the ratio value of signal intensity of test zone/reference zone is reduced (FIG. 2a).

2-2. PSA Detection Using Method of Present Invention

A PSA detection experiment was conducted as follows using the method for detecting an antigen of the present invention.

The experiment was conducted by the same method as in example 2-1 above, and the same sample was used.

Figure 2B:
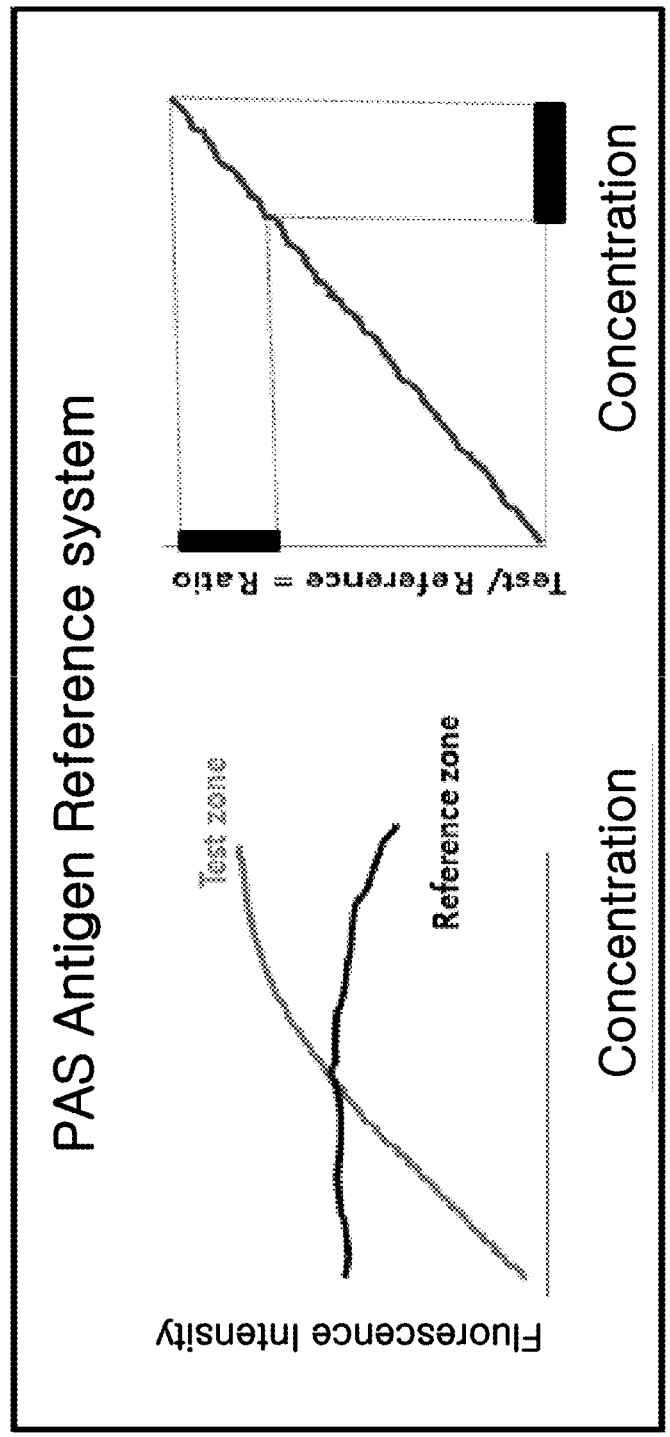
FIG. 2b are graphs respectively showing (i) signal intensities of a test zone and a reference zone according to the concentration of an analysis sample and (ii) a ratio value of signal intensity of test zone/reference zone according to the concentration of the analysis sample, using a prostate specific antigen (PSA) reference system using the method of the present invention.

As a result, it could be confirmed that, as the concentration of the analysis sample becomes higher, the ratio value of signal intensity of test zone/reference zone constantly increases, showing a linear proportional graph (FIG. 2b).

Example 3: Comparison of Detection Data According to Measurement Temperature

A comparison test was conducted using the method for detecting an antigen of the present invention and the conventional method for detecting an antigen (Rabbit IgG reference system).

3-1. PSA Detection Using Conventional Method for Detecting Antigen

For a reference value for PSA detection results according to the method of the present invention, a PSA detection experiment was conducted as follows.

Among the samples used in the present invention, a patient sample having a concentration on a linear section was used, and the experiment was conducted in temperature environments of 13.8° C., 24.2° C., and 29.7° C., respectively. After chips were previously set according to the respective temperatures, 30 μl of a sample (patient serum or plasma with or without lipoprotein lipase) was dropped around the sample inlet of a chip. Five minutes after the sample was dropped, the chip was inserted into the apparatus for detecting an antigen according the present invention. After about 40 seconds, the degree of presence of prostate specific antigen in the sample was quantitatively displayed on the display screen, and the signal intensity values of the test zone and the reference zone were also displayed.

Figure 3A:
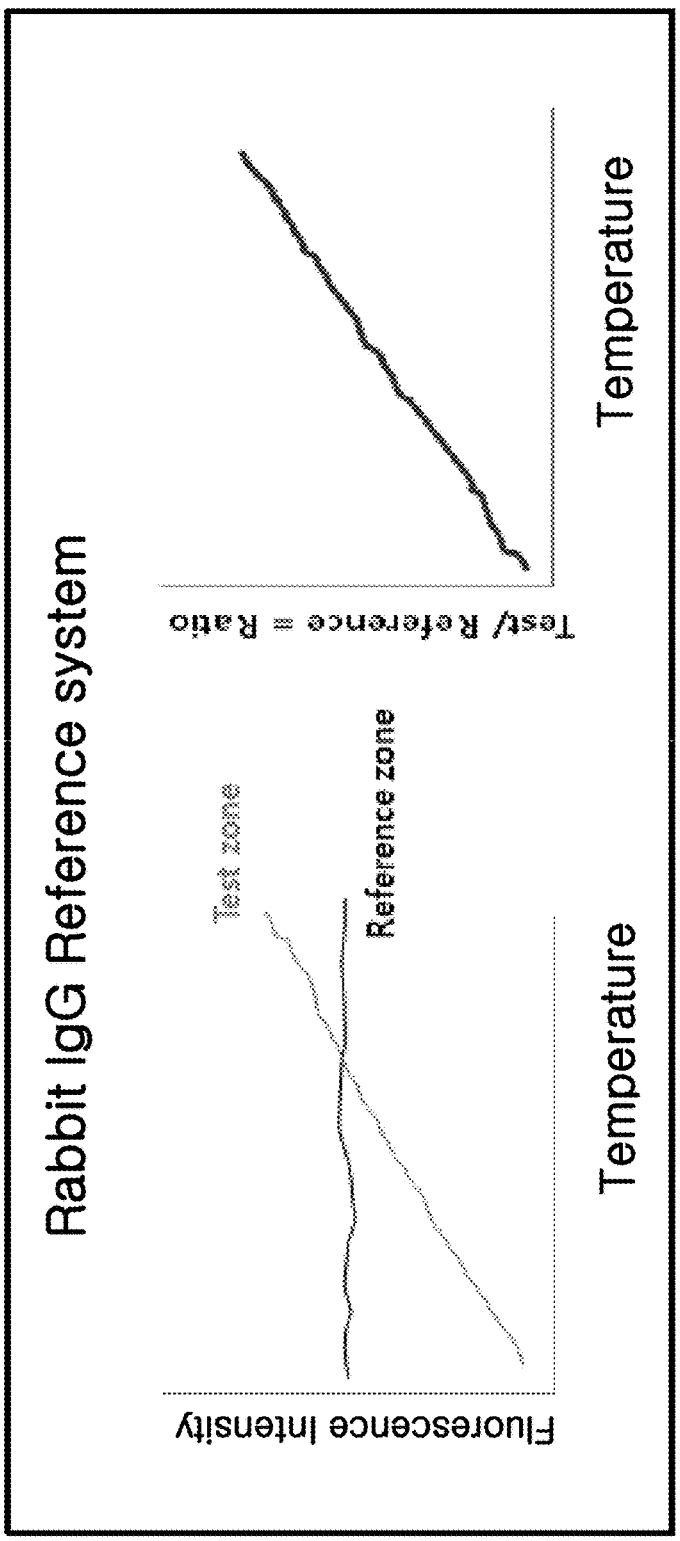
FIG. 3a are graphs respectively showing (i) signal intensities of a test zone and a reference zone according to the measurement temperature and (ii) a ratio value of signal intensity of test zone/reference zone according to the measurement temperature, using a Rabbit IgG reference system.
Figure 3B:
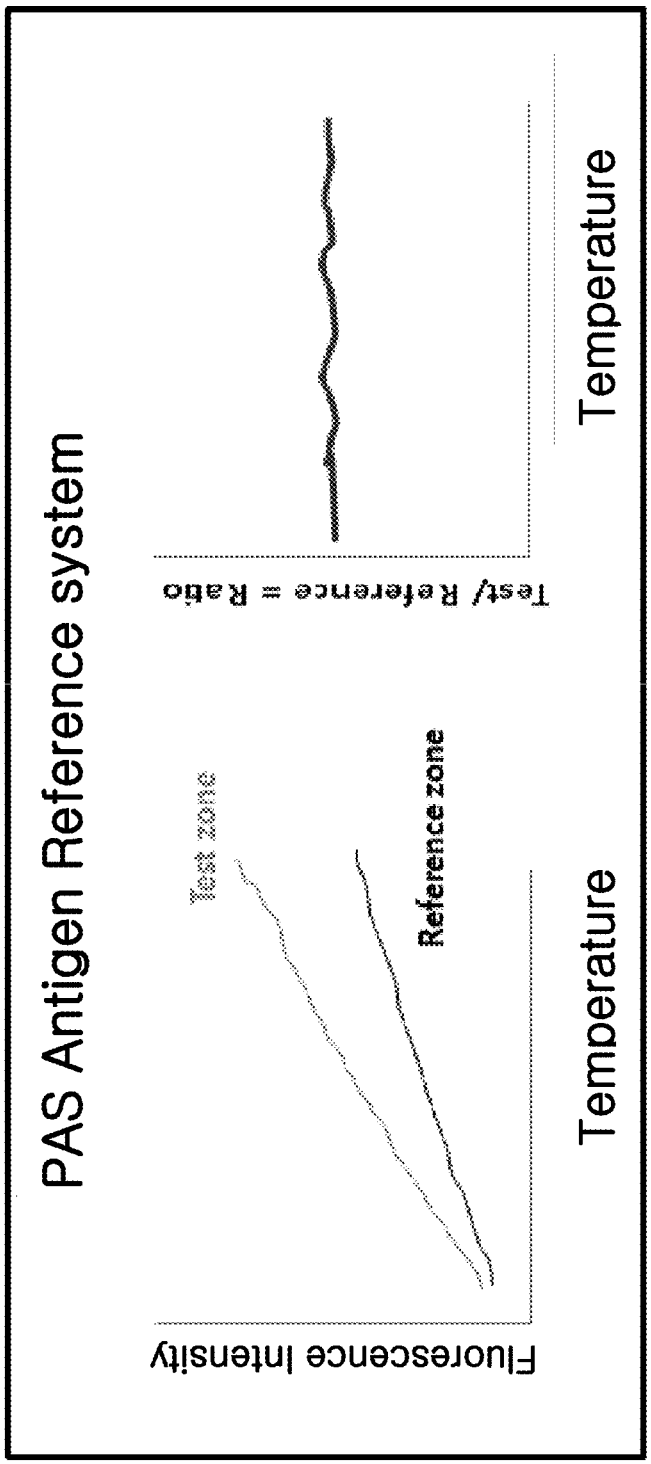
FIG. 3b are graphs respectively showing (i) signal intensities of a test zone and a reference zone according to the measurement temperature and (ii) a ratio value of signal intensity of test zone/reference zone according to the measurement temperature, using a prostate specific antigen (PSA) reference system.

As a result, it could be confirmed that, as the measurement temperature became higher, the ratio value of signal intensity of test zone/reference zone increased (FIG. 3a). Therefore, it was confirmed that the antigen-antibody reaction increased according to the temperature.

3-2. PSA Detection Using Method of Present Invention

A PSA detection experiment was conducted as follows, using the method for detecting an antigen of the present invention.

The experiment was conducted by the same method as in example 3-1 above, and the same sample was used.

As a result, it could be confirmed that the ratio value of signal intensity of test zone/reference zone was almost constantly maintained (FIG. 3a).

Example 4: Measurement of Coefficient of Variation According to Temperature for the Same Sample In order to confirm whether the method for detecting an antigen of the present invention is influenced by temperature, an experiment of measuring the coefficient of variation according to temperature was conducted. A comparison test was conducted using the Rabbit IgG reference system, the Taq IgG reference system, the method for detecting an antigen of the present invention (PSA standard system), and the method for detecting an antigen by Biosite company (U.S. Pat. No. 6,194,222).

The experiments were conducted by the same method as in example 3-1 above, and the same sample was used.

Figure 4A:
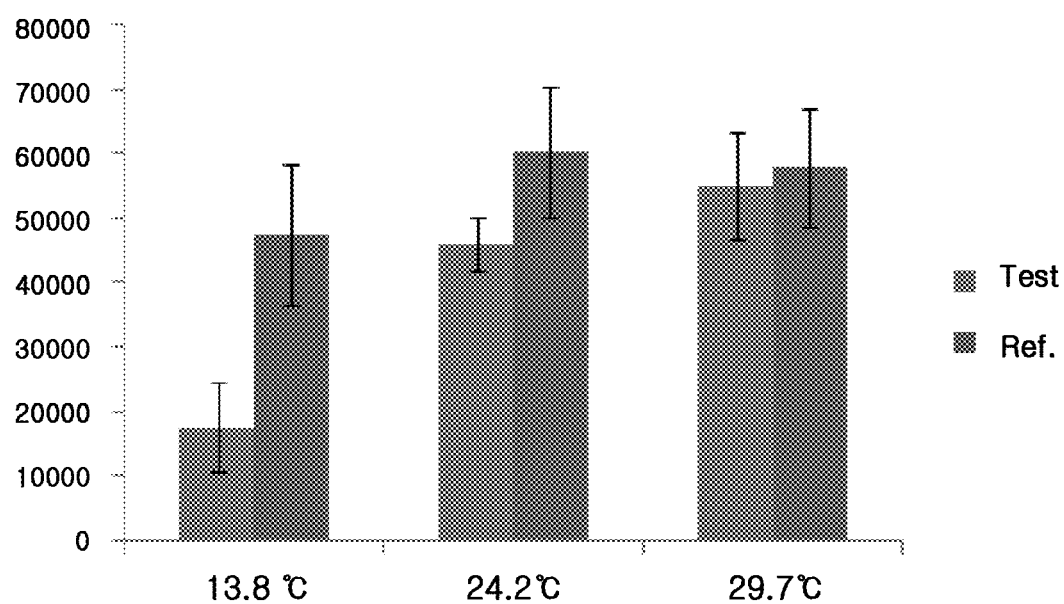
FIG. 4 are graphs showing (i) signal intensities of a test zone and a reference zone according to the measurement temperature (FIG. 4a) and (ii) a ratio value of signal intensity of test zone/reference zone according to the measurement temperature (FIG. 4b), using the conventional method for detecting an antigen (Rabbit-Goat anti-Rabbit system).
Figure 4B:
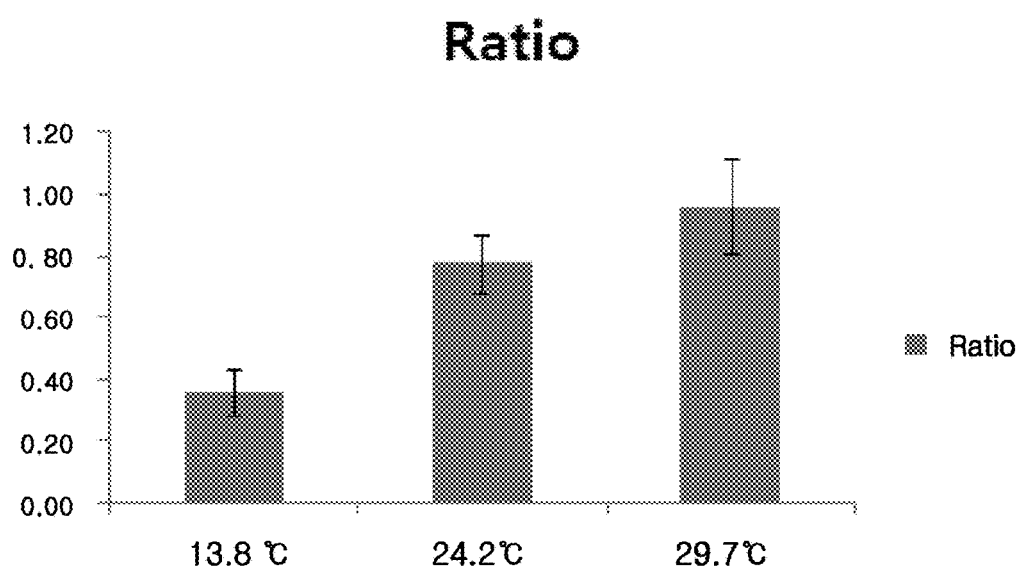
Figure 5A:
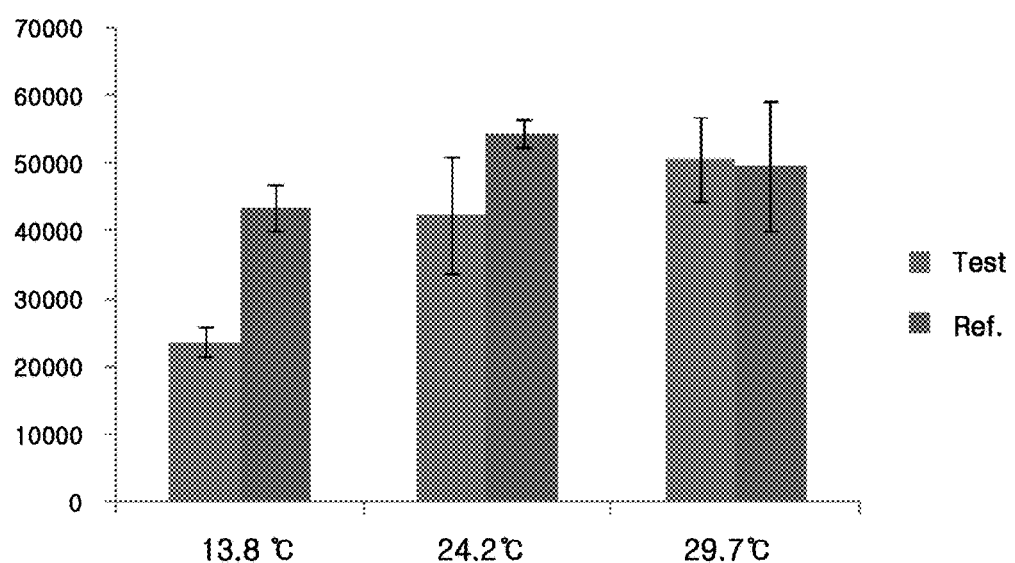
FIG. 5 are graphs showing (i) signal intensities of a test zone and a reference zone according to the measurement temperature (FIG. 5a) and (ii) a ratio value of signal intensity of test zone/reference zone according to the measurement temperature (FIG. 5b), using the conventional method for detecting an antigen (Taq-Mouse anti-Taq system).
Figure 5B:
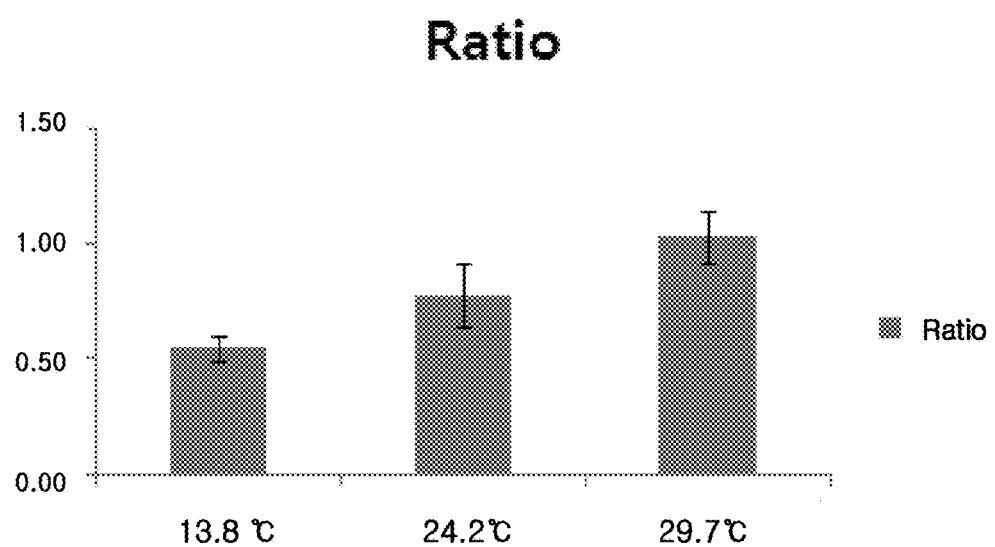
Figure 6A:
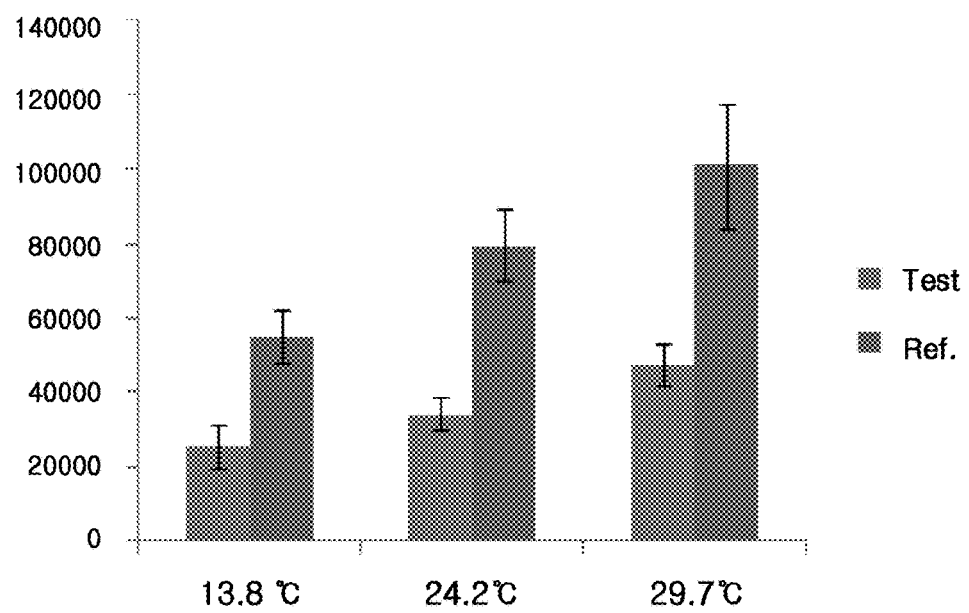
FIG. 6 are graphs showing (i) signal intensities of a test zone and a reference zone according to the measurement temperature (FIG. 6a) and (ii) a ratio value of signal intensity of test zone/reference zone according to the measurement temperature (FIG. 6b), using a method for detecting an antigen using the method of the present invention (PSA-Mouse anti-PSA system).
Figure 6B:
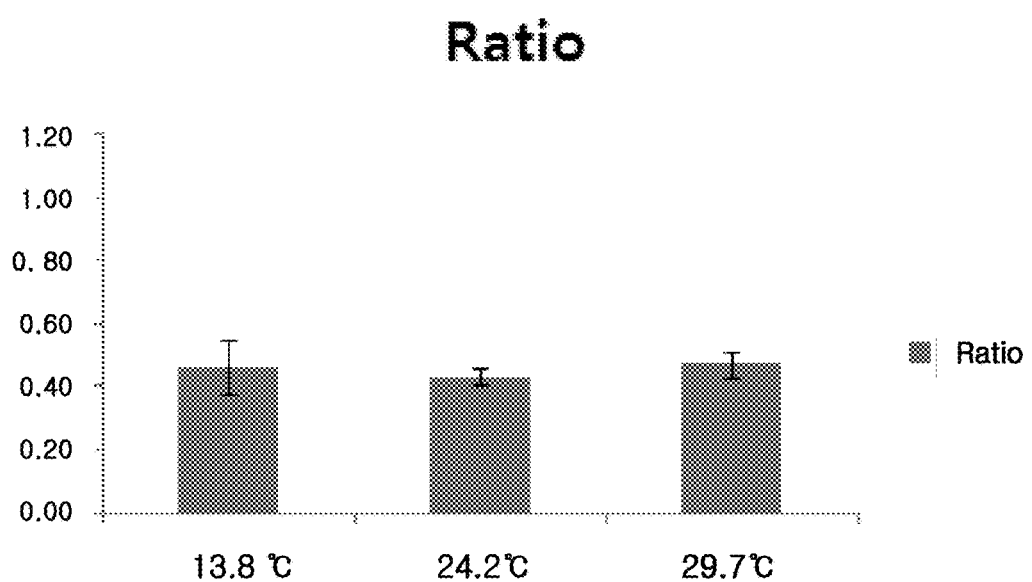
Figure 7:
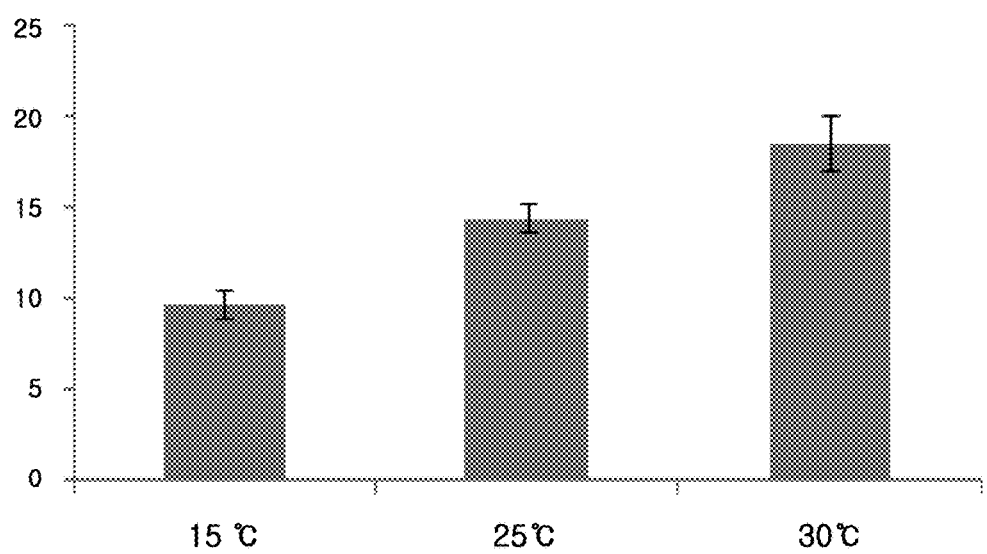
FIG. 7 is a graph showing a ratio value of signal intensity of test zone/reference zone according to the measurement temperature using a method for detecting an antigen by Biosite company.

Signals of the test zone and the reference zone were measured at three temperatures, and expression values thereof were calculated to express on a graph. The expression values were calculated as follows. A reference substance specifically reacting with only the test zone was used at different concentrations to prepare a standard concentration graph. A function corresponding to the graph was input into a code chip of the apparatus for detecting an antigen, which is used in the present invention. As a result, the expression value for the concentration corresponding to the signal generated from the test zone was calculated (Tables 4 and 5). As a result, when the Rabbit IgG reference system (FIGS. 4a and 4b, coefficient of variation according to temperature: 33%), Taq IgG reference system (FIGS. 5a and 5b, coefficient of variation according to temperature: 36.9%), and the detection method by the Biosite company (FIG. 7, coefficient of variation according to temperature: 31.0%) were used, it could be confirmed that as the measurement temperature increased, the ratio value of signal intensity of test zone/reference zone increased, and thus the amount of PSA detected was varied with the temperature change. While, when the method of the present invention was used, the expression values of PSA were measured to be 4.35, 4.01, and 4.45 at 13.8° C., 24.2° C., and 29.7° C., respectively. Therefore, the method of the present invention was shown to be hardly influenced by the temperature change (FIGS. 6a and 6b, coefficient of variation according to temperature: 5.5%).

$$\text{Coefficient of variation} = \text{Standard deviation}/\text{Average} \times 100 \quad [\text{Equation 6}]$$

TABLE 4

Confirmation on coefficient of variation according to temperature by detection method of present invention

| Temperature | 13.8° C. | 24.2° C. | 29.7° C. |
|---|---|---|---|
| 1. Rabbit - Goat anti Rabbit | | | |
| Test zone (T) | 17508 | 46064.8 | 54976.6 |
| Reference zone (R) | 47493.8 | 60212.6 | 57960.8 |
| Ratio (T/R) | 0.36 | 0.78 | 0.96 |
| Ratio expression value | 3.25 | 7.94 | 10.32 |
| Coefficient of variation according to temperature | | 33% | |
| 2. Taq - Mouse anti Taq | | | |
| Test zone (T) | 23712.8 | 42231.4 | 50583 |
| Reference zone (R) | 43406.2 | 54236.2 | 49724.5 |
| Ratio (T/R) | 0.55 | 0.78 | 1.03 |
| Ratio expression value | 5.27 | 7.94 | 11.28 |
| Coefficient of variation according to temperature | | 36.9% | |

TABLE 4-continued

Confirmation on coefficient of variation according to temperature by detection method of present invention

| Temperature | 13.8° C. | 24.2° C. | 29.7° C. |
|---|---|---|---|
| 3. Rabbit - Goat anti Rabbit | | | |
| Test zone (T) | 25488.4 | 34305.2 | 47303.0 |
| Reference zone (R) | 54916.4 | 79658.4 | 100845.4 |
| Ratio (T/R) | 0.46 | 0.43 | 0.47 |
| Ratio expression value | 4.35 | 4.01 | 4.45 |
| Coefficient of variation according to temperature | | 5.5% | |

TABLE 5

Confirmation on coefficient of variation according to temperature by Biosite analysis

| No. of Measurement of ratio (T/R) expression value | 14° C. | 24.8° C. | 29.6° C. |
|---|---|---|---|
| 1 | 10.1 | 15.1 | 19.8 |
| 2 | 9.87 | 15.3 | 17.5 |
| 3 | 8.69 | 14.6 | — |
| 4 | 9.32 | 13.5 | 19.9 |
| 5 | 10.7 | 13.8 | 17.1 |
| Average | 9.736 | 14.46 | 18.575 |
| Standard deviation | 0.765983 | 0.789303 | 1.481834 |
| Coefficient of variation (CV %) | 7.867533 | 5.45853 | 7.977574 |

Example 5: Comparison 1 on Detection Data of High-Concentration Analysis Sample A comparison test on the resolution of measurement result values when an analysis sample has a high concentration was conducted using the detection method of the present invention and the conventional detection method (Rabbit IgG reference system). Human seminal fluid (BiosPacific, J63000) was used as a PSA antigen, and the experiment method was the same as in example 2.

FIG. 6 shows results obtained by measuring a ratio value of signal intensity of test zone/reference zone according to the concentration of the analysis sample, using the prostate specific antigen (PSA) reference system using the method of the present invention.

TABLE 6

Confirmation on signal intensity according to PSA concentration

| PSA concentration (ng/ml) | Test zone (Tz) | Reference zone (Rz) | T/R ratio |
|---|---|---|---|
| 0.45 | 1385 | 63039 | 0.02 |
| 5.9 | 22764 | 73660 | 0.31 |
| 11.7 | 26354 | 48260 | 0.55 |
| 23.4 | 61881 | 57307 | 1.08 |
| 46.9 | 80387 | 64155 | 1.25 |
| 93.8 | 85358 | 47459 | 1.80 |
| 188 | 127889 | 51162 | 2.50 |
| 375 | 156706 | 42899 | 3.65 |
| 750 | 168668 | 29439 | 5.73 |
| 1500 | 140212 | 16517 | 8.49 |

Figure 8:
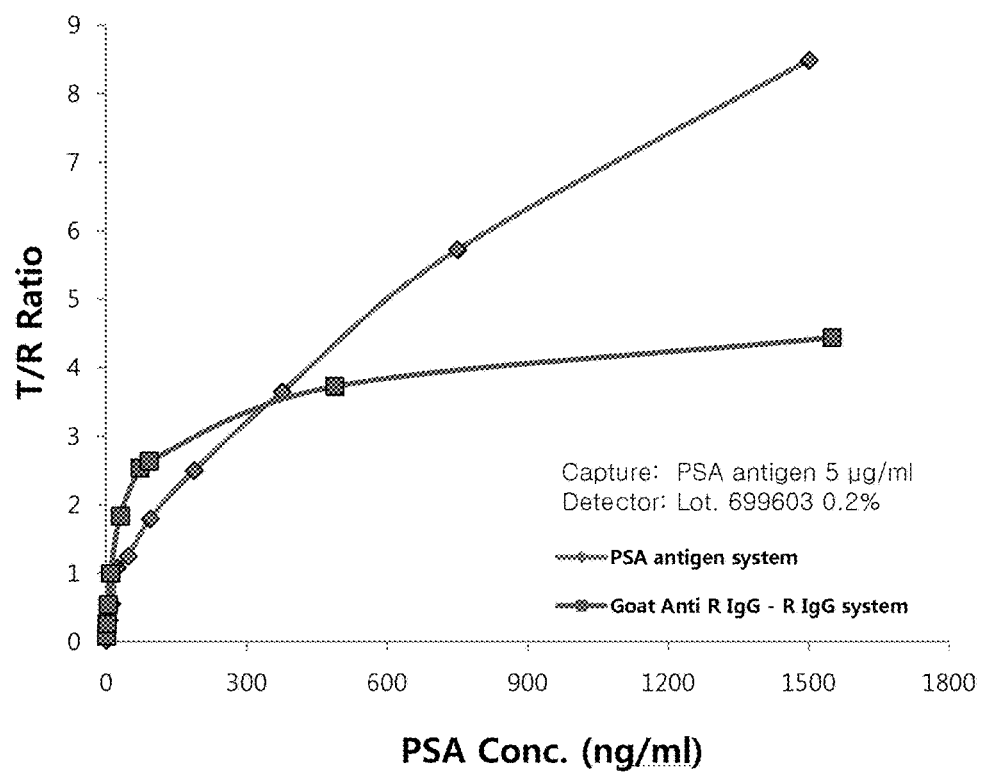
FIG. 8 is a graph showing a ratio value of signal intensity of test zone/reference zone according to the concentration of an analysis sample, using a prostate specific antigen (PSA) reference system using the method of the present invention.

As shown in FIG. 8, when the conventional Goat anti R IgG-R IgG system was used, as the concentration of the analysis sample increased, the increase in the ratio value of signal intensity of test zone/reference zone decreased, and since the slope of the graph rapidly decreases at PSA concentrations of 100 ng/ml or more, quantitative analysis was impossible for the antigen of 100 ng/ml or more (FIG. 8).

However, it could be confirmed that, when the method of the present invention was used, the quantitative detection of the sample was possible even at a concentration of 1500 ng/ml, and when the graph of FIG. 8 was used, the detection of antigen was possible even at concentrations of 1500 ng/ml or more.

Example 6: Comparison 2 on Detection Data of High-Concentration Analysis Sample

A comparison test on the resolution of measurement result values when an analysis sample has a high concentration was conducted using the detection method of the present invention and the conventional detection method (Rabbit IgG reference system). As a high-concentration PSA sample, a sample which was verified to have 8720 ng/mL, which was measured by Beckman Coulter UNICELL DXI 800, Access Hybritech PSA, was used, and the experiment method was the same as in example 2 above.

Figure 9A:
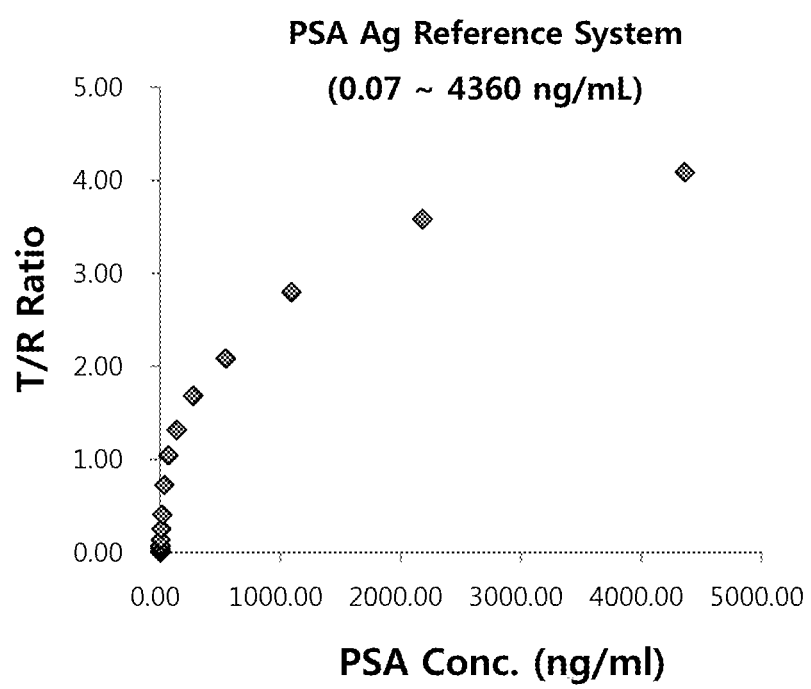
FIGS. 9a and 9b are graphs respectively showing ratio values of signal intensity of test zone/reference zone of a high-concentration analysis sample, using a prostate specific antigen (PSA) reference system using the method of the present invention (FIG. 9a) and the conventional method for detecting an antigen (Rabbit-Goat anti-Rabbit system) (FIG. 9b).
Figure 9B:
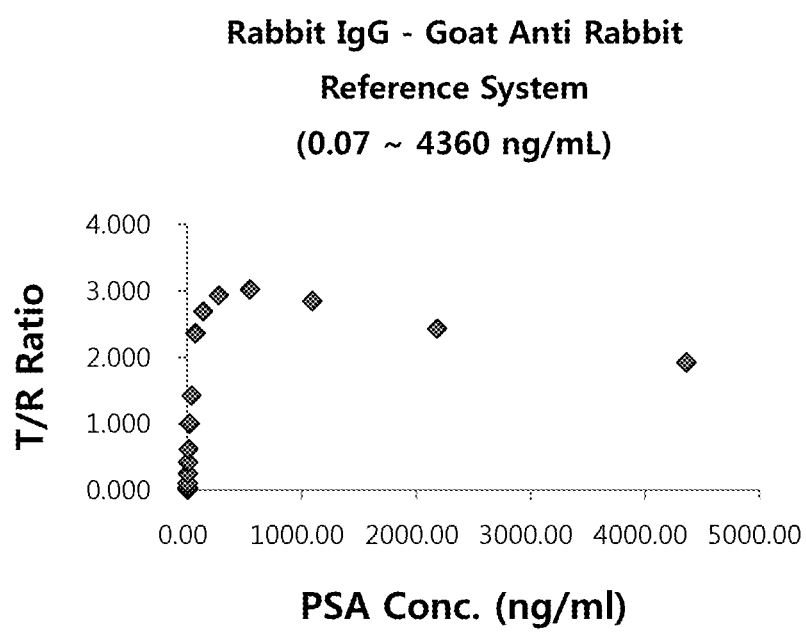

FIGS. 9a and 9b show results obtained by measuring the ratio values of signal intensity of test zone/reference zone according to the PSA concentration, using the PSA reference system using the method of the present invention and the conventional method for detecting an antigen (Rabbit IgG reference system). Table 7 shows an average of measurement values obtained by measuring the signal for each sample twice.

As shown in FIG. 9 and Table 7, the detection/measurement of PSA of 4360 ng/mL was possible for the method of the present invention (FIG. 9a), but in the conventional Goat anti R IgG-R IgG system, the hook effect was shown when the concentration of antigen was 272.5 ng/mL or more, and thus quantitative analysis of antigen was impossible (FIG. 9b).

TABLE 7

Confirmation on signal intensity according to PSA concentration

| PSA concentration (ng/ml) | Method of present invention T/R Ratio | Rabbit IgG reference system T/R Ratio |
|---|---|---|
| 0.07 | 0.00 | 0.008 |
| 0.13 | 0.01 | 0.015 |
| 0.27 | 0.01 | 0.032 |
| 0.53 | 0.02 | 0.046 |
| 1.06 | 0.04 | 0.108 |
| 2.13 | 0.08 | 0.253 |
| 4.26 | 0.14 | 0.425 |
| 8.52 | 0.25 | 0.620 |
| 17.03 | 0.41 | 1.007 |
| 34.06 | 0.73 | 1.427 |
| 68.13 | 1.05 | 2.364 |
| 136.25 | 1.32 | 2.694 |
| 272.50 | 1.69 | 2.934 |
| 545.00 | 2.09 | 3.023 |
| 1090.00 | 2.80 | 2.849 |
| 2180.00 | 3.58 | 2.434 |
| 4360.00 | 4.09 | 1.927 |

Having described a preferred embodiment of the present invention, it is to be understood that variants and modifications thereof falling within the spirit of the invention may become apparent to those skilled in this art, and the scope of this invention is to be determined by appended claims and their equivalents.

The invention claimed is:

1. A method for detecting an antigen in an analysis sample, the method comprising:
    (a) contacting an analysis sample with a detection antibody to which a marker generating a detectable signal is attached and which specifically binds to the antigen;
    (b) contacting a capture antibody with the resultant product of step (a), the capture antibody specifically binding to the antigen to be detected and being bound to a test zone;
    (c) contacting the detection antibody, to which the marker generating a detectable signal is attached, with a reference substance which is bound to a reference zone and which includes an epitope to which the detection antibody specifically binds;
    (d) measuring signals generated from the markers of the resultant product of step (b) and the resultant product of step (c); and
    (e) analyzing the measured signals to determine the presence or absence and amount of the antigen in the analysis sample,
    wherein steps (a) to (d) or steps (b) to (d) are performed on a microchip having a microchannel, wherein the analyzing of the measured signals is performed by measuring signals of a reaction start zone, the test zone, the reference zone, and a reaction end zone, which are provided in the microchannel in said order and through each of which the sample passes, wherein the reaction start zone and the reaction end zone are parts of sections obtained by dividing a signal measurement area in the microchannel into predetermined intervals, and
    wherein the analyzing of the measured signals further includes an analysis step of calculating the error rate of the signals measured, the error rate being calculated by measuring signals of the reaction start zone and the reaction end zone which are positioned from the test zone and the reference zone at a predetermined distance.

2. The method of claim 1, wherein the capture antibody is bound to the surface of a solid substrate formed on the test zone of the microchannel.

3. The method of claim 2, wherein a continuous reaction occurs among the analysis sample, the detection antibody, the capture antibody and the reference substance on the solid substrate surface formed in the microchannel of one microchip.

4. The method of claim 2, wherein the microchannel of the microchip includes the test zone and the reference zone which are provided in the solid substrate, and the capture antibody being bound to a surface of the test zone.

5. The method of claim 4, wherein the analysis sample is applied to the microchip, the applied analysis sample being contacted with the test zone and the reference zone through the flow thereof formed in the microchannel.

6. The method of claim 5, wherein the analysis sample is sequentially contacted with the test zone and the reference zone or sequentially contacted with the reference zone and the test zone.

7. The method of claim 1, wherein the reference substance includes the same material as the antigen or a fragment of the antigen including the epitope.

8. The method of claim 1, wherein, in the analyzing of the measured signals, the ratio value of intensities of the signals generated from the markers of the resultant product of step (b) and the resultant product of step (c) is calculated.

9. The method of claim 1, wherein, when the error rate calculated from the reaction start zone and the reaction end zone is 20% or higher, the analyzing of the signals is again conducted, the error rate being calculated by [|(signal of reaction start zone−signal of reaction end zone) signal of reaction start zone]×100.

10. The method of claim 1, wherein the analysis sample is whole blood, plasma, serum, body fluid, or cell culture supernatant.

11. The method of claim 1, wherein the antigen is drug, toxin, autoantibody, autoantigen, protein, carbohydrate, nucleic acid, or cancer-related antigen.

12. The method of claim 11, wherein the antigen is a cancer-related antigen.

13. The method of claim 8, wherein the ratio value of intensities of the signals generated from the markers of the resultant product of step (b) and the resultant product of step (c) is not influenced by a change in the temperature at which the method is conducted.

14. The method of claim 13, wherein the ratio value of intensities of the signals generated from the markers of the resultant product of step (b) and the resultant product of step (c) is constant at a temperature range of 10-30° C. at which the method is conducted.

15. The method of claim 13, wherein the ratio value of intensities of the signals generated from the markers of the resultant product of step (b) and the resultant product of step (c) is linearly proportional to the concentration of the analysis sample of step (a).

* * * * *